United States Patent
Røhr et al.

(10) Patent No.: US 9,612,162 B2
(45) Date of Patent: Apr. 4, 2017

(54) TIME-TEMPERATURE INDICATOR SYSTEM

(75) Inventors: Åsmund K. Røhr, Oslo (NO); Peder Oscar Andersen, Oslo (NO); Brit Salbu, Oslo (NO); Eggert F. Gudjonsson, Oslo (NO); Marit Nandrup Pettersen, Askim (NO); Christian Salbu Aasland, Oslo (NO)

(73) Assignee: KEEP-IT TECHNOLOGIES AS, Oslo (NO)

( * ) Notice: Subject to any disclaimer, the term of this patent is extended or adjusted under 35 U.S.C. 154(b) by 699 days.

(21) Appl. No.: 14/112,031

(22) PCT Filed: Apr. 10, 2012

(86) PCT No.: PCT/NO2012/050060
§ 371 (c)(1),
(2), (4) Date: Dec. 18, 2013

(87) PCT Pub. No.: WO2012/141594
PCT Pub. Date: Oct. 18, 2012

(65) Prior Publication Data
US 2014/0098834 A1    Apr. 10, 2014

(30) Foreign Application Priority Data
Apr. 15, 2011 (NO) .................................. 20110590

(51) Int. Cl.
*G01K 3/00* (2006.01)
*G01K 3/04* (2006.01)
*G01N 31/22* (2006.01)

(52) U.S. Cl.
CPC ............. *G01K 3/04* (2013.01); *G01N 31/229* (2013.01)

(58) Field of Classification Search
None
See application file for complete search history.

(56) References Cited

U.S. PATENT DOCUMENTS 3,194,072 A    7/1965  Vaala
3,946,611 A    3/1976  Larsson
(Continued)

FOREIGN PATENT DOCUMENTS

EP    505449 A1    9/1992
EP    1 312 918    5/2003
(Continued)

OTHER PUBLICATIONS

International Preliminary Report on Patentability received for PCT Patent Application No. PCT/NO2012/050059, issued on Jun. 10, 2013, 12 pages.
(Continued)

*Primary Examiner* — Erica Lin
(74) *Attorney, Agent, or Firm* — Morrison & Foerster LLP

(57) ABSTRACT

The present invention relates to a time-temperature indicator system useful for monitoring the time and temperature exposure of foods, nutraceuticals, pharmaceuticals, cosmetics, chemicals and other products. The system provides improved time-temperature sensitivity and a response which better reflects that of the reactions leading to quality loss of the monitored product. Further, the invention also relates to a combination comprising said time-temperature indicator system and a product storage container. A method for producing said time-temperature indicator system is also part of the present invention.

15 Claims, 4 Drawing Sheets

(56) References Cited

U.S. PATENT DOCUMENTS

| | | | |
|---|---|---|---|
| 3,967,579 | A | 7/1976 | Seiter |
| 4,045,383 | A | 8/1977 | Koff |
| 4,154,107 | A | 5/1979 | Giezen et al. |
| 4,452,995 | A | 6/1984 | Patel et al. |
| 4,834,017 | A | 5/1989 | Favetto et al. |
| 5,053,339 | A | 10/1991 | Patel |
| 6,054,318 | A | 4/2000 | Murray et al. |
| 7,290,925 | B1* | 11/2007 | Skjervold ............ G01N 31/229 116/216 |
| 2004/0115319 | A1* | 6/2004 | Morris ................. B65B 25/001 426/231 |
| 2004/0253733 | A1 | 12/2004 | Prusik et al. |
| 2006/0063140 | A1 | 3/2006 | Nussinovitch et al. |
| 2007/0036038 | A1 | 2/2007 | Ambrozy et al. |
| 2008/0023362 | A1 | 1/2008 | Genosar |
| 2008/0241932 | A1* | 10/2008 | Kendig ................. G01N 33/02 436/2 |
| 2011/0106000 | A1* | 5/2011 | Jones ...................... A23B 4/16 604/23 |

FOREIGN PATENT DOCUMENTS

| | | |
|---|---|---|
| EP | 1333262 A1 | 8/2003 |
| EP | 1 598 667 | 11/2005 |
| EP | 1882919 A2 | 1/2008 |
| GB | 2430257 A | 3/2007 |
| JP | 1-141976 A | 6/1989 |
| JP | 2009-298470 A | 12/2009 |
| WO | 91/09287 A1 | 6/1991 |
| WO | 01/26993 A1 | 4/2001 |
| WO | 01/27608 A2 | 4/2001 |
| WO | WO-01/26993 | 4/2001 |
| WO | WO-01/27608 | 4/2001 |
| WO | 01/64430 A1 | 9/2001 |
| WO | WO-01/64430 | 9/2001 |
| WO | 03/007088 A2 | 1/2003 |
| WO | 2005/075978 A2 | 8/2005 |
| WO | 2005/078402 A1 | 8/2005 |
| WO | 2006/021953 A2 | 3/2006 |
| WO | 2008/083926 A1 | 7/2008 |
| WO | 2009/127529 A1 | 10/2009 |
| WO | 2010/102721 A1 | 9/2010 |

OTHER PUBLICATIONS

International Written Opinion received for PCT Patent Application No. PCT/NO2012/050059, mailed on Feb. 15, 2013, 7 pages.
International Written Opinion received for PCT Patent Application No. PCT/NO2012/050060, mailed on Jul. 18, 2012, 7 pages.
Dranca et al., "Thermal Stability of Gelatin Gels: Effect of Preparation Conditions on the Activation Energy Barrier to Melting", Polymer, vol. 50, 2009, pp. 4859-4867.
Rohr et al., U.S. Appl. No. 14/112,024, filed Dec. 18, 2013, titled "Time-Temperature Indicator System I", 33 pages.
Norwegian Search Report received for Norwegian Patent Application No. 20110589, mailed on Nov. 15, 2011, 2 pages.
Norwegian Search Report received for Norwegian Patent Application No. 20110590, mailed on Nov. 15, 2011, 2 pages.
International Search Report received for PCT Patent Application No. PCT/N02012/050059, mailed on Feb. 15, 2013, 5 pages.
International Preliminary Report on Patentability received for PCT Patent Application No. PCT/N02012/050060 mailed on May 7, 2013, 6 pages.
International Search Report received for PCT Patent Application No. PCT/NO2012/050060 mailed on Jul. 18, 2012, 4 pages.
Labuza, T. P., "Application of Chemical Kinetics to Deterioration of Foods", Journal of Chemical Education, vol. 61, No. 4, Apr. 1984, pp. 348-358.
McMeekin et al., "Predictive Microbiology: Theory and Application", Research Studies Press Ltd., 1993, 12 pages.
Wanihsuksombat et al., "Development and Characterization of a Prototype of a Lactic Acid-Based Time-Temperature Indicator for Monitoring Food Product Quality", Journal of Food Engineering, vol. 100, 2010, pp. 427-434.
Yan et al., "Development and Characterization of a New Amylase Type Time-Temperature Indicator", Food Control, vol. 19, 2008, pp. 315-319.
Non Final Office Action received for U.S. Appl. No. 14/112,024, mailed on Jul. 25, 2016, 15 pages.
Extended European Search Report dated Jan. 18, 2017, directed to EP Application No. 16185235.5; 9 pages.

* cited by examiner

TIME-TEMPERATURE INDICATOR SYSTEM

CROSS REFERENCE TO RELATED APPLICATIONS

This application is a U.S. National Phase patent application of PCT/NO2012/050060, filed on Apr.; 10, 2012, which claims priority to Norwegian Patent Application No. 20110590, filed on Apr. 15, 2011, each of which is hereby incorporated by reference in the present disclosure in its entirety.

FIELD OF THE INVENTION

The present invention relates to a time-temperature indicator system useful for monitoring the time and temperature exposure of foods, nutraceuticals, pharmaceuticals, cosmetics, chemicals and other products. The system provides improved time-temperature sensitivity as compared to existing time-temperature indicators, time-temperature sensitivity control and a response which better reflects that of the reactions leading to quality loss of the monitored product. Further, the invention also relates to a combination comprising said time-temperature indicator system and a product storage container or a bag closure device. A method for producing said time-temperature indicator system is also part of the present invention.

BACKGROUND OF THE INVENTION

The quality of food products and other perishables are highly dependent on storage conditions such as the temperature and the storage time from production or packing until it finally reaches the end consumer. The deterioration processes are faster when the temperature is raised due to increasing biochemical or physical reaction rates, and therefore the quality of perishable goods declines more rapidly at high temperatures than at low temperatures.

Examples of perishable goods which need to be stored under conditions such that a particular temperature exposure limit is not exceeded or at least not exceeded for longer than a predetermined period of time, include fresh food products, chilled food products and food products that have been pre-cooked or processed by freezing, irradiation, partial cooking, freeze drying or steaming, including products being packages in vacuum packaging, MAP-packed packaging or other industrial packaging methods. Further examples of products which may need to be stored under appropriate temperature conditions are certain pharmaceuticals, e.g. insulin, vaccines and concentrated omega-3 products; certain nutraceuticals, e.g. supplement oils, e.g. fish oil, and vitamins; chemicals; veterinary products and certain cosmetics; which would otherwise deteriorate.

Currently date marking is the standard method applied for the insurance of storage quality. By date marking only, no information is given to the consumer or others about the storage conditions to which the product has been exposed; hence the purchasers of susceptible products are not able to determine whether the product has been stored under appropriate temperature conditions during the time of storage. Relying on date marking as a sole quality criterion presupposes that the perishable product has been stored under appropriate conditions throughout the entire storage period. To be on the safe side, producers of perishable goods often use date marking with a wide safety margin, hence products which are actually still suitable for consumption or use are often discarded.

Therefore, there is a continuing interest in the monitoring of the time and temperature to which storage sensitive products have been exposed in e.g. food, pharmaceutical and chemical distribution chains from factory to consumer.

By supplying a perishable product with a time-temperature indicator which follows the individual product from packing to sale, the producer, the grosser, the retailer and the consumer will have a better product control than they currently have. By the use of a time-temperature indicator which matches the characteristics of investigated products, the true shelf life of the products can be monitored, which means that discarding can be delayed until the applied time-temperature indicator has detected that storage conditions based on time and temperature have not been appropriate and/or exceeded.

In theory, time-temperature indicators may be classified as either partial history or full history indicators depending on their response mechanism. Partial history indicators will typically not respond unless a threshold temperature has been exceeded, while full history indicators typically respond independently of a temperature threshold and provides a cumulative response to the time and temperature to which the time-temperature indicator (and hence the product) has been exposed.

EP 505 449 (Tepnel Medical) discloses an example of a partial history time-temperature indicator comprising a fusible material such as polycaprolactone triol, polyethylene glycol C1-4 alkyl ether and polyvinyl alcohol, which flows when a given threshold temperature is exceeded and re-solidifies when exposed to temperatures below the same temperature. The fusible material flows in a substrate and an indicator system produces a physically detectable change in the substrate when the fusible material flows therein.

U.S. Pat. No. 7,290,925 (TimeTemp) discloses an example of a full history time-temperature indicator where the response given by the time-temperature indicator is easily read by the human eye, and in conjunction with a product it gives a measure of the storage conditions to which the product has been exposed by giving a cumulative response to time-temperature exposure.

The reliability of a time-temperature indicator depends to a large extent on the correlation of the time-temperature indicator response with that of reactions leading to quality loss. Unless the change in the rate with temperature of the time-temperature indicator system closely parallels the temperature dependence of the rate of quality detoriation of the monitored product, the system will not be able to accurately predict the shelf life remaining for a variable temperature distribution. Also, as the temperature dependence on quality detoriation may be different in different temperature intervals, the temperature dependency of the time-temperature indicator may in these cases advantageously be of a non-linear response.

Further, the response to time and temperature should be substantially irreversible to prevent the time-temperature indicator from being reset. It is also preferred that the time-temperature indicator is capable of indicating the time-temperature history within a wide temperature range. The indicator should also be conveniently activated so that pre-usage storage of the indicator is not a problem, and the response to time and temperature should be given in a visually and easily interpretable manner. Finally, and importantly, it should be non-toxic and not pose any threat to human health.

According to the present invention there is now provided a time-temperature indicator system useful for monitoring the time and temperature exposure of food and other products. The system provides improved time-temperature sensitivity within a wide temperature range and a response which better reflects that of the reactions leading to quality loss.

SUMMARY OF THE INVENTION

A first aspect of the present invention relates to a time-temperature indicator system, comprising a first compartment adjacent to a separate second compartment; said first compartment comprising at least one agent which changes visual appearance upon reduction; said second compartment comprising at least one mobile agent; said first and second compartments initially being separated by suitable means for preventing contact between the at least one agent which changes visual appearance upon reduction and the at least one mobile agent; the system being activated by bringing said two compartments into contact and thereby allow for the at least one mobile agent to migrate into the first compartment; with the proviso that
i) at least one of said mobile agents is a pH modifying agent; and
said first compartment further comprises a mutarotational reducing agent; or
ii) at least one of said mobile agents is a mutarotational reducing agent.

A second aspect of the present invention relates to a combination, comprising the system according to the first aspect of the present invention and a product storage container or a bag closure device.

A third aspect of the present invention relates to a time-temperature indicator system, comprising an absorptive material; wherein i) at least one agent which changes visual appearance upon reduction has been absorbed to said absorptive material; the system being activated by absorbing at least one mutarotational reducing agent to said absorptive material; or ii) at least one mutarotational reducing agent and at least one agent which changes visual appearance upon reduction have been absorbed to said absorptive material; the system being activated by absorbing at least one pH modifying agent.

A fourth aspect of the present invention relates to a method for producing the time-temperature indicator system according to the first aspect of the present invention, the method comprising the following steps:
i) forming at least a first and a second separate compartments in a plastic sheet layer,
ii) filling said first compartment with a composition comprising an agent which changes visual appearance upon reduction;
iii) filling said second compartment with a composition comprising the the mobile agent(s) defined according to the first aspect of the present invention;
iv) sealing said compartments by a second layer;
v) optionally, activating said device by selectively compressing at least one compartment formed by the two layers thus bringing the two compartments into contact.

Preferred embodiments of the present invention are set forth below and in the dependent claims.

DESCRIPTION OF THE FIGURES

Preferred embodiments of the present invention will now be illustrated in more detail with reference to the accompanying figures.

DETAILED DESCRIPTION OF THE INVENTION

Figure 1:
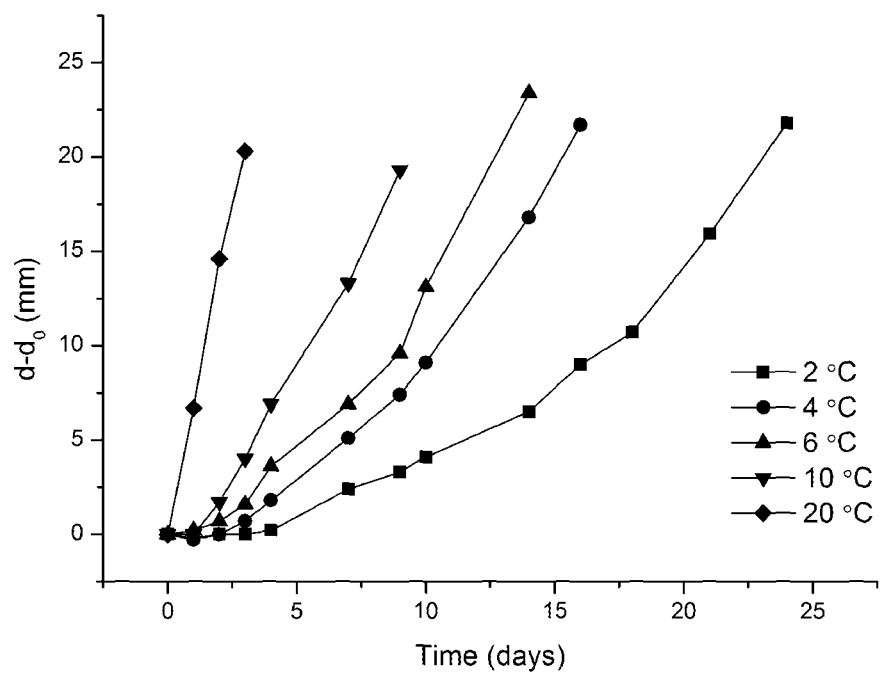
FIG. 1 illustrates the time-temperature sensitivity of the system at specific temperatures and how the time-temperature sensitivity changes with temperature. Y-axis: Position of the moving front "d" which is given with reference to the initial boundary between the second compartment and the first compartment "$d_0$". X-axis: Number of days.

A perfect time-temperature indicator should have a response which closely parallels the temperature dependence of the rate of quality detorioation of the monitored product. Further, the response to time and temperature should be substantially irreversible to prevent the time-temperature indicator from being reset. It is also preferred that the time-temperature indicator is capable of indicating the time-temperature history within a wide temperature range. The indicator should also be conveniently activated so that pre-usage storage of the indicator is not a problem, and the response to time and temperature should be given in a visually and easily interpretable manner. Finally, and importantly, it should be non-toxic and not pose any threat to human health.

A number of time-temperature indicators have been provided during the recent years, but none of them seem to fulfil each and one of the above features. In particular it has proven difficult to provide a time-temperature indicator having a response which closely parallels the temperature dependence of the rate of quality detoriation of the monitored product within a wide temperature range. Such an indicator should typically have low temperature sensitivity within a certain temperature range and very high temperature sensitivity outside this temperature range.

Until now, the main focus of the prior art has been on identifying processes which have a suitable time-temperature sensitivity within a certain temperature range and how to design a time-temperature indicator based on one such process that is visually and easily interpretable. Even though relatively good indicators have been provided, the indicators have shown to be too simple to closely parallel the temperature dependence of the rate of quality detoriation of the monitored product within a wide temperature range.

Surprisingly it has now been discovered that the mutarotation process has a suitable time-temperature sensitivity and that the time-temperature sensitivity of the process is easily modifiable by pH adjustment to better reflect the temperature dependence of the rate of quality detoriation of the monitored product within a wide temperature range (see example 1-3 and 6). Even though an indicator based exclusively on that process is an improvement over the prior art, an even better indicator may be provided by designing a system based on a combination of at least two time-temperature sensitive processes, e.g mutarotation and diffusion.

The result of the discovery is an improved time-temperature indicator system which has:
   a response which closely parallels the temperature dependence of the rate of quality detoriation of the monitored product within a wide temperature range;
   a response to time and temperature which is substantially irreversible to prevent the time-temperature indicator from being reset;
   an activation system which see to that pre-usage storage of the indicator is not a problem;
   a response to time and temperature that is given in a visually and easily interpretable manner;
   ingredients and reaction products that are non-toxic and not pose any threat to human health.

A first aspect of the present invention relates to a time-temperature indicator system, comprising a first compartment adjacent to a separate second compartment; said first compartment comprising at least one agent which changes visual appearance upon reduction; said second compartment comprising at least one mobile agent; said first and second compartments initially being separated by suitable means for preventing contact between the at least one agent which changes visual appearance upon reduction and the at least one mobile agent; the system being activated by bringing said two compartments into contact and thereby allow for the at least one mobile agent to migrate into the first compartment; with the proviso that
i) at least one of said mobile agents is a pH modifying agent; and
   said first compartment further comprises a mutarotational reducing agent; or
ii) at least one of said mobile agents is a mutarotational reducing agent.

The term "agent which changes visual appearance upon reduction" refers to an agent which changes visual appearance, e.g. a change in color, upon reduction. One example of such an agent is starch-complexed iodine which upon reduction changes color from dark blue to transparent/colorless. Ferroin is an example of a pH independent agent which upon reduction changes colour from slightly blue to red and methylene blue is an example of a pH dependent agent which changes colour from blue to colourless upon reduction. Other suitable agents which changes colour upon reduction are 2,2'-Bipyridine (Ru or Fe complexes); Nitroferroin; 5,6-Dimethylferroin; Phenylanthranilic acid; Ethoxy chrysoidine; o-Dianisidine; Sodium diphenylamine sulfonate; Viologen; Diphenylbenzidine; Diphenylamine; Sodium 2,6-Dibromophenol-indophenol; Sodium 2,6-Dichlorophenol-indophenol; Sodium o-Cresol indophenol; Thionine; Indigotetrasulfonic acid; Indigotrisulfonic acid; Indigo carmine; Indigomono sulfonic acid; Phenosafranin; Safranin; Neutral red; variamine blue; potassium permanganate; xylenol orange; and xylene cyanol.

The term "mobile agent" refers to an agent which migrates into said first compartment upon activation of the system.

The term "pH modifying agent" refers to an agent which is able to change the pH of the surrounding environment. Examples of a pH modifying agent is a buffer, e.g. an alkaline buffer; weak or strong base; and weak or strong acid. Of particular interes are alkaline buffers such as carbonate buffers, e.g. sodium carbonate buffer or a potassium carbonate buffer.

In one preferred embodiment according to the present invention, the pH modifying agent prior to activation of the system is present at a concentration which is in the range 0.001-1 M, e.g. 0.01-1M, 0.05-1M, 0.1-1M or 0.5-1M.

Figure 11:
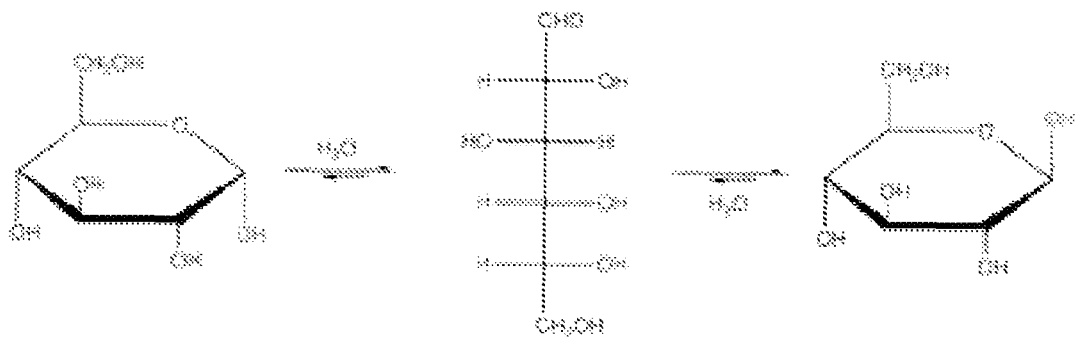
FIG. 11 illustrates reversible epimerization of α-D-glucose to β-D-glucose via the open-chain form.

The term "mutarotational agent", refers to an agent which is able to undergo mutarotation. Mutarotation is the change in the optical rotation that occurs by epimerization, that is the change in the equilibrium between two epimers (diastereomers that differ in configuration of only one stereogenic center) when the corresponding stereocenters interconvert. For example, cyclic sugars show mutarotation as $\alpha$ and $\beta$ anomeric forms interconvert (see FIG. 11).

The term "reducing agent", refers to the compound in a reduction-oxidation (redox) reaction that donates one or more electrons to another species.

The term "mutarotational reducing agent", refers to an agent which is able to undergo mutarotation and which also is able to donate an electron or electrons to another specie in a reduction-oxidation reaction. A typical example of compounds having these characterisitics are reducing sugars. A sugar is only a reducing sugar if it has an open chain with an aldehyde or a ketone group (see FIG. 11).

The system is activated by bringing said two compartments into contact, e.g. by removing or breaking the sealing between the compartments, and thereby allow for the at least one mobile agent to migrate into the first compartment. In one preferred embodiment, said sealing is a peelable layer between two plastic layers.

In one embodiment according to the first aspect of the present invention, at least one of said mobile agents is a mutarotational reducing agent. When the system is activated, the mutarotational reducing agent migrates into the first compartment containing the agent which changes visual appearance upon reduction. Preferably, the mutarotational reducing agent migrates into the first compartment in a time-temperature dependent manner.

In order for the mutarotational reducing agent to be able to donate electrons to the agent which changes visual appearance upon reduction, the mutarotational reducing agent must have an open chain with an aldehyde or a ketone group. This is typically the case for the intermediate product of a mutarotation process (see FIG. 11).

The mutarotation process rate is both dependent on temperature and pH. By increasing the temperature and/or pH, more intermediate products (open chain with an aldehyde or a ketone group) are formed resulting in an increased redox reaction rate. Said intermediate products then donate electrons to the agent which changes visual appearance upon reduction.

Since the mutarotation process rate is dependent on pH, the pH of the first compartment may be adjusted to fine tune the time-temperature indicator system of the present invention. Optionally, a pH modifying agent may be included in the second compartment to fine tune the time-temperature indicator system of the present invention.

If at least one of said mobile agents is a mutarotational reducing agent, the pH of the first compartment prior to activation should be >7, more preferably >7.5, even more preferably >8, such as e.g. a pH >8.5, and most preferably the pH of the first compartment prior to activation should be >9.

Optionally, if at least one of said mobile agents is a mutarotational reducing agent and the pH of the first compartment is <9, e.g. <8.5, <8, <7.5 or <7 prior to activation, it is preferred that the pH of the second compartment prior to activation is >8, more preferably >8.5, even more preferably >9 but always higher than the pH in the first compartment.

What is of importance in case at least one of said mobile agents is a mutarotational reducing agent is that the pH of the first and second compartments are adjusted to make sure that the mutarotational reducing agent once entered the first compartment is able to reduce the agent which changes visual appearance upon reduction.

In another embodiment according to the first aspect of the present invention, at least one of said mobile agents is a pH modifying agent; and said first compartment further comprises a mutarotational reducing agent.

When the system is activated, the pH modifying agent migrates into the first compartment containing i) the agent which changes visual appearance upon reduction; and ii) the mutarotational reducing agent. Preferably, the pH modifying agent migrates into the first compartment in a time-temperature dependent manner.

In order for the mutarotational reducing agent to be able to donate electrons to the agent which changes visual appearance upon reduction, the mutarotational reducing agent must have an open chain with an aldehyde or a ketone group. This is typically the case for the intermediate product of a mutarotation process (see FIG. 11).

The mutarotation process rate is both dependent on temperature and pH. By increasing the temperature and/or pH, more intermediate products (open chain with an aldehyde or a ketone group) are formed resulting in an increased redox reaction rate.

However, at low pH the mutarotation process is so slow that almost no intermediate products are formed.

Accordingly, in those cases where the mutarotational reducing agent is present in the first compartment together with the agent which changes visual appearance upon reduction, it is preferred that the pH of the first compartment prior to activation is <9, more preferably <8.5, even more preferably <8 or <7.5 and most preferably <7. The pH of the second compartment prior to activation is preferably >8 but always higher than the pH in the first compartment.

What is of importance in case the mutarotational reducing agent is present in the first compartment together with the agent which changes visual appearance upon reduction is that i) the pH of the first compartment prior to activation does not allow significant mutarotation to occur; and that ii) the pH of the first and second compartments are adjusted to allow the mutarotational reducing agent to reduce the agent which changes visual appearance upon reduction once the pH modifying agent enters said first compartment.

As soon as the pH modifying agent enters said first compartment, the pH is starting to rise resulting in an increase in the mutarotation reaction rate of the mutarotational reducing agent. As a consequence, more intermediate products are formed (open chain with an aldehyde or a ketone group) resulting in an increased redox reaction rate. Said intermediate products then donate electrons to the agent which changes visual appearance upon reduction.

Since the mutarotation process rate is dependent on pH, the pH of the first compartment and/or the amount/kind of pH modifying agent in the second compartment may be adjusted to fine tune the time-temperature indicator system of the present invention.

In another embodiment according to the present invention, a matrix is contained within said first compartment.

In one embodiment according to the present invention the agent which changes visual appearance upon reduction is immobilized within a matrix contained in said first compartment. Even though the agent may have some degree of mobility (migration) within the immobilizing material, the migration is very restricted. In one preferred embodiment, the agent which changes visual appearance upon reduction is immobilized within the immobilizing material.

As used herein, "a substantially immobilized agent" is intended to include an agent which is significantly less mobile (reduced migration) than said mobile agent. In one embodiment, the substantially immobilized agent has at least 50% reduced migration, preferably at least 60% reduced migration, more preferably at least 70% reduced migration, even more preferably at least 80% reduced migration, most preferably at least 90% reduced migration, e.g. 95%, 96%, 97%, 98% or 99% (e.g. 99.2%, 99.6%, 99.8% or 100% reduced migration) as compared to the mobile agent under similar conditions.

In one preferred embodiment, said matrix comprises at least a first matrix component; said first matrix component being a colloid polymer, preferably a colloid gel-forming polymer. Said colloid polymer may be either a reversible or an irreversible colloid polymer. In one embodiment said matrix consists of said first matrix component.

In case the first matrix component is an irreversible polymer, it may be irreversibly set prior to activation by processes such as ionic interactions, or it may be irreversibly set after activation by ionic interactions occurring due to ions diffusing from the first compartment to the second compartment. Examples of irreversibly set gels are polymers such as i) anionic polymers, e.g. alginates or pectins combined with polyvalent metal ions such as $Ca^{2+}$, $Cu^{2+}$. $Fe^{2+}$, $Ba^{2+}$; or ii) cationic polymers such as chitosans combined with ions such as $SO_4^{2-}$ or polyphosphates.

A reversible polymer is a polymer that exists as a solution (sol state) or as a solid jelly-like material (gel state) depending on the imposed conditions. In case the first matrix component is a reversible polymer, it is preferred that it does not enter sol state during activation of the system, more preferably also does not enter sol state after the system has been activated.

In one embodiment, the melting point of the first matrix component is in the range 0-100° C., more preferably in the range 10-100° C., even more preferably in the range 20-100° C. and most preferably in the range 30-100° C. e.g. in the range 40-100° C., in the range 50-100° C., in the range 60-100° C., in the range 70-100° C., in the range 80-100° C. or in the range 90-100° C.

Optionally, said first matrix component is a reversible polymer which has a melting point above −30° C., above −20° C. or above −10° C., preferably above 0° C., more preferably above 10° C., even more preferably above 20° C. and most preferably above 30° C. such as e.g. above 40° C., above 50° C., above 60° C., above 70° C., above 80° C. or above 90° C.

The melting point of a gel is the temperature at which it changes state from gel to liquid, enters gel-sol transition. The melting point of a substance depends (usually slightly) on pressure, but is herein intended to be defined at standard atmospheric pressure if not otherwise specified. Most of the commercially available polymers have a well defined melting point. However, there also exist a number of different techniques for measuring the melting point of a gel, including differential scanning calorimetry (DSC). If not otherwise specified herein, the referred melting points are measured by using differential scanning calorimetry (Polymer 50 (2009) 4859-4867).

The concentration of the first matrix component should preferably be in the range 0.01-30% by weight, more preferably in the range 0.1-20% by weight, even more preferably in the range 0.1-15% by weight and most preferably in the range 0.1-10% by weight, e.g. in the range 0.1-5% by weight or in the range 0.1-2% by weight. Said concentration being calculated as the quantity of solid polymer as compared to the total weight of the ingredients including the solid polymer.

Further, the gel forming polymer of the first matrix component may be in the form of a synthetic or natural colloid gel-forming polymer, or a combination thereof; or more preferably in the form of a synthetic or natural hydrocolloid gel-forming polymer, or a combination thereof. In the case of a hydrocolloid gel-forming polymer, the hydrocolloid preferably being selected from the group consisting of an alginate, such as Na-alginate, alginic acid or propylene glycol alginate; a carrageenan (e.g Kappa, Iota, or Lambda carrageenan, refined or semi-refined); an agar or agarose, a gum, a cellulose (such as CMC, HPMC, MC), starches containing amylase and/or amylopectin, starch derivatives such as carboxymethyl, carboxyethyl or carboxypropyl starch, starch esters such as starch acetates and a protein (such as gelatine from mammals or fish, e.g gelatine from cold water or tropical water fish), or salts and derivatives thereof. Other non-gel forming polymers may also be added to the system in order to control viscosity; in order to change surface tension; in order to aid in immobilization of the immobilized agent etc.

In a presently preferred embodiment of the invention as described herein, said first matrix component is a gel forming polymer, preferably a reversible gel forming polymer, which provides improved time-temperature sensitivity to the system within a wide temperature range and a response which better reflects that of the reactions leading to quality loss of the monitored product.

In one preferred embodiment, wherein the agent which changes visual appearance upon reduction is a starch-iodine complex, the matrix (preferably gelatine) contained in the first compartment has been subjected to iodination. By using iodinated matrix, any unwanted reactions between iodine and gelatine is reduced to a minimum. A method for preparing iodinated gelatine is disclosed in example 6.

In case the matrix comprises a plurality of matrix components, it is preferred that said matrix is formed by mixing the matrix components when in their sol state, more preferably by mixing the matrix components when in their sol state and then allow at least one of said matrix components to undergo sol-gel transition.

In another preferred embodiment according to the present invention, said matrix comprises at least a first matrix component; said first matrix component being a paste.

Pastes typically consist of a suspension of granular material in a background fluid. The individual grains are jammed together like sand on a beach, forming a disordered, glassy or amorphous structure, and giving pastes their solid-like character. It is this "jamming together" that gives pastes some of their most unusual properties; this causes paste to demonstrate properties of fragile matter.

Said paste preferably being selected from the group consisting of petroleum jelly with zinc oxide, clay and silica gel paste.

In another preferred embodiment according to the present invention, said matrix comprises at least a first matrix component; said first matrix component being a gum.

Said gum preferably being selected from the group consisting of locust (carob) bean gum, xanthan gum, guar gum, gum arabic (acacia gum), gum ghatti, gum tragacanth; even more preferably said gum is locust (carob) bean gum (example 7).

Locust bean gum occurs as a white to yellow-white powder. It consists chiefly of high-molecular-weight hydrocolloidal polysaccharides, composed of galactose and mannose units combined through glycosidic linkages, which may be described chemically as galactomannan. It is dispersible in either hot or cold water, forming a sol having a pH between 5.4 and 7.0, which may be converted to a gel by the addition of small amounts of e.g. sodium borate.

In another preferred embodiment according to the present invention, said matrix comprises at least a first matrix component; said first matrix component being an emulsion, preferably an oil-in-water emulsion or a water-in-oil emulsion, with a mayonnaise or paste like consistency.

An emulsion is a mixture of two or more liquids that are normally immiscible (un-blendable). Emulsions are part of a more general class of two-phase systems of matter called colloids. Although the terms colloid and emulsion are sometimes used interchangeably, emulsion is used when both the dispersed and the continuous phase are liquid. In an emulsion, one liquid (the dispersed phase) is dispersed in the other (the continuous phase).

As previously disclosed, the mutarotation process rate is both dependent on temperature and pH. By increasing the temperature and/or pH, more intermediate products (open chain with an aldehyde or a ketone group) are formed resulting in an increased redox reaction rate. Said intermediate products then donate an electron to the agent which changes visual appearance upon reduction.

In one preferred embodiment, the redox reaction between the mutarotational reducing agent and the agent which changes visual appearance upon reduction is substantially irreversible, preferably irreversible.

Said mutarotational reducing agent preferably being selected from a reducing sugar, a mixture of reducing sugars, a non-reducing sugar which can be converted to a reducing sugar by tautomerization or a mixture of non-reducing sugars which can be converted to reducing sugars by tautomerization.

The term "tautomerization", refers to the chemical reaction where tautomers, isomers of organic compounds, readily interconvert. It is common that this reaction results in the formal migration of a hydrogen atom or proton, accompanied by a switch of a single bond and adjacent double bond. The concept of tautomerizations is called tautomerism.

Said sugar is preferably selected from a monosaccharide, disaccharide, trisaccharide, oligosaccharide, polysaccharide or any mixture thereof.

More preferably the mutarotational reducing agent is a reducing sugar selected from the group consisting of glucose, fructose, glyceraldehyde, galactose, lactose and maltose; or any mixture thereof. In a particularily preferred embodiment, the mutarotational reducing agent is glucose.

In one preferred embodiment, the mutarotational reducing agent prior to activation of the system is present at a concentration which is in the range 0.001-1 M, preferably in the range 0.005-1M, more preferably in the range 0.01-1M, even more preferably in the range 0.05-1M and most preferably in the range 0.5-1M.

As previously discussed, the mutarotational reducing agent must have an open chain with an aldehyde or a ketone group in order to be able to donate electrons to the agent which changes visual appearance upon reduction.

Figure 6:
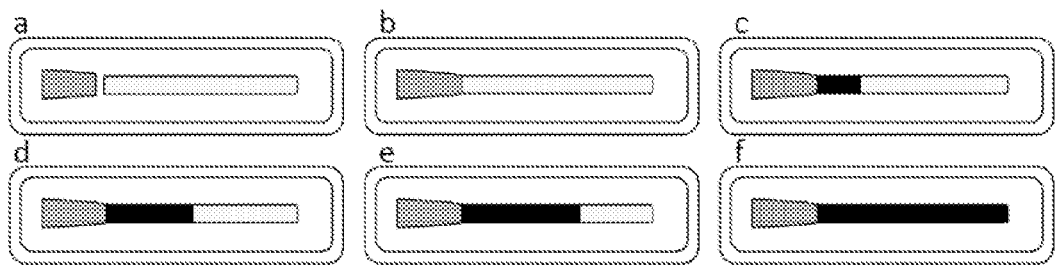
FIG. 6 illustrates one embodiment of the time-temperature indicator system according to the present invention: (a) before activation; (b) immediately after activation; (c-f) colour developing reaction.
Figure 7:
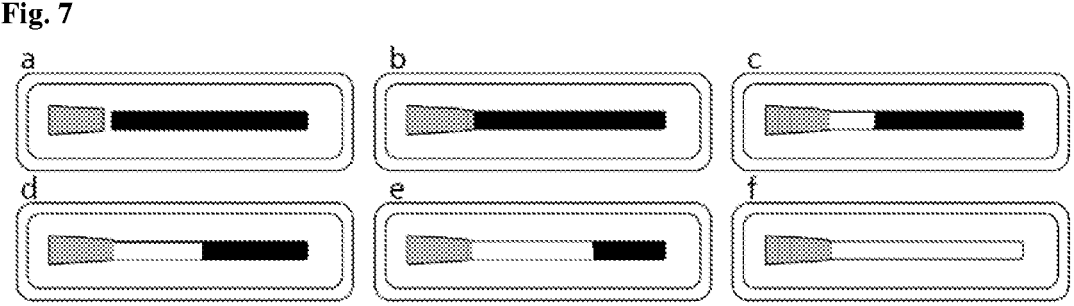
FIG. 7 illustrates one embodiment of the time-temperature indicator system according to the present invention: (a) before activation; (b) immediately after activation; (c-f) colour fading reaction.

In one preferred embodiment, said agent which changes visual appearance upon reduction is reduced by the mutarotational reducing agent when brought in contact with each other. Said change in visual appearance preferably being a color change, either fading of color (FIG. 7) or formation of color (FIG. 6).

Said agent which changes visual appearance upon reduction preferably being colorless in its oxidized state and colored in its reduced state; or colored in its oxidized state and colorless in its reduced state.

In one preferred embodiment, the agent which changes visual appearance upon reduction is a starch-iodine complex.

In one preferred embodiment, the agent which changes visual appearance upon reduction prior to activation of the system is present at a concentration which is in the range 0.001-1 M, preferably in the range 0.005-1M, more preferably in the range 0.01-1M, even more preferably in the range 0.05-1M and most preferably in the range 0.5-1M.

It is also within the scope of the invention that the above system can be associated with, integrated with or incorporated in a product storage container. Thus, a second aspect of the present invention relates to a combination comprising the system according to the present invention and a product storage container.

Products that may be contained in said product storage container includes e.g. food products, chemical products, pharmaceutical products, veterinary products, cosmetics or biological materials. Typically such food products are products which are fresh, frozen, preserved or dehydrated, and typical biological materials are products like e.g. diagnostic reagents, blood and blood components, plants, seeds and semen. The system is preferably attached to an inner or outer surface of the product storage container, optionally integrated in the material of the product storage container. Typical containers are e.g. cans, cartons, flasks, trays, bags and jars, said containers being in example MAP-packed or vacuum packed.

The association of the system to such containers can be provided by means of an adhesive layer on the system by which the system will be substantially irremovable when associated with the container. The association of the system to the container can be constructed in such a way that if the system is attempted to be removed from the container by which it is associated, it will break or be destroyed. By this it can prevented that the system is tampered with.

Figure 8:
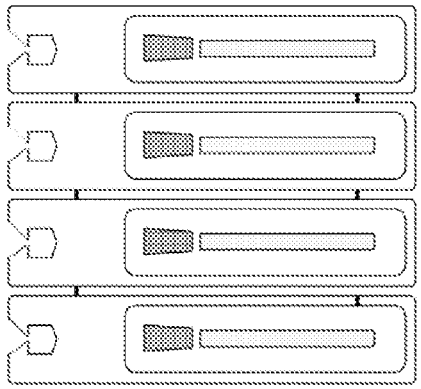
FIG. 8 illustrates one embodiment of the combination according to the present invention comprising the time-temperature indicator system and a bag closure device.
Figure 9:
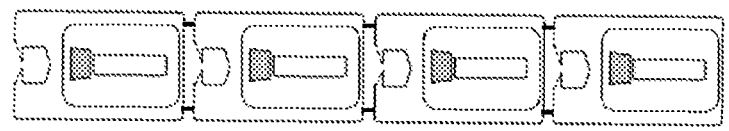
FIG. 9 illustrates one embodiment of the combination according to the present invention comprising the time-temperature indicator system and a bag closure device.

It is also within the scope of the invention that the above system can be associated with, integrated with or incorporated in a bag closure device (FIGS. 8 and 9). Thus, a further aspect of the present invention relates to a combination comprising the system according to the present invention and a bag closure device.

A further aspect of the present invention relates to a bag closure time-temperature indicator device (FIG. 8, FIG. 9), comprising a time-temperature indicator associated with, integrated with or incorporated in a bag closure device, said time-temperature indicator being capable of detecting the time and temperature exposure for a product and provides a visually detectable signal that indicates the time-temperature history of the monitored product. Preferably, said time-temperature indicator device is not activated by opening the bag. Preferably, said bag closure time-temperature indicator device does not comprise any means for activating the time-temperature indicator. Preferably said time-temperature indicator provides a visual indication of the time-temperature history of the product within said bag from the time of packing onwards.

The bag closure time-temperature indicator may be of particular use for products wherein there is a technical difficulty, or cost related difficulty, in attaching the indicator to product bag as a separate device. The bag closure time-temperature indicator has several technical benefits, and may give advantages such as being able to both close a product bag and provide a means for measuring the time-temperature exposure for the product in a one-step procedure which is both cost effective and time effective. It also eliminates the need for providing first a bag closures and second a separate time-temperature indicator to the product.

The bag closure time-temperature indicator may be provided as a single unit prior to attachment to the product packaging, and can be
  a) produced by a combined process wherein the closure device is part of the same structure as the indicator for measuring the time and temperature exposure, such that the supporting structure plate for the indicator also provides the structure used in the closure device; i.e. being a polymer based structure, such as a plastic material comprising a PP, PE, PET or laminate plastics, capable of providing structure to the entire device; or
  b) produced separately, such that the closure device and the indicator for measuring the time and temperature exposure is combined in a separate step prior to attachment, such combining method comprising glue, welding, stitching, or other conventional means for combining materials; or
  c) produced by a method comprising the steps of
    i) forming at least a first and a second separate compartments in a plastic sheet layer,
    ii) forming the plastic sheet layer into a bag closure device suitable for closing a product bag;
    iii) filling said first compartment with a composition comprising an agent which changes visual appearance upon reduction;
    iv) filling said second compartment with a composition comprising the the mobile agent(s) defined in claim 1;

v) sealing said cavities by a enclosing cavities with a second layer;

vi) optionally, activating said device by selectively compressing at least one compartment formed by the two layers thus bringing the two compartments into contact. In one preferred embodiment step vi) is mandatory.

In one embodiment the bag closure time-temperature indicators may be attached to each other end-to-end (FIG. 9) or attached to each other side-by-side (FIG. 8) prior to activation and attachment to the bag. The chain of bag closure time-temperature indicators may preferably consist of the same base structure, wherein the structure is cut such that there are thin residual attachment points or strings between each device. The chain of indicators are preferably broken during the attachment process, i.e. by mechanical, heating or irradiational stress to the chain.

The bag closure time-temperature indicator may be square; rectangular; rectangular with rounded corners; with a length of up to 4 mm; 8 mm; 20 mm; 30 mm; 40 mm; 80 mm; 160 mm or above; with width of up to 1 mm; 2 mm; 4 mm; 6 mm; 8 mm; 10 mm; 20 mm; 30 mm; 40 mm; 80 mm; or above with height of up to 0.1 mm; 0.5 mm; 1 mm; 2 mm; 4 mm; 6 mm; 10 mm or above; and may be triangular, wave-shaped, curved, sinusoidal, leaf like; circular, oval, elliptical; cylindrical; pentagonic, diamond, tear-dropped, trapezoidal, symmetrical or non-symmetrical; or combinations thereof, and may further comprise an area which is cut out in order to provide sufficient properties for closing a product bag.

The time-temperature indicator region of the bag closure time-temperature indicator may be triangular, wave-shaped, curved, sinusoidal, leaf like; circular, oval, elliptical; cylindrical; pentagonic, diamond, tear-dropped, trapezoidal, symmetrical or non-symmetrical; or combinations thereof; and may comprise one or more regions of indication.

The device may comprise a polymeric structure said structure comprising polystyrene (PS), polypropylene (PP) and/or polyester materials such as polyethylene terephthalate (i.e. crystalline; oriented or amorphous); PVC=Poly Vinyl Chloride; Expanded Polystyrene; SBS=Solid Bleached Sulfate paperboard; paperboard; HDPE=High or low density Polyethylene (HDPE/LDPE), however a preferred structure may comprise a PET laminate structure or PVC.

The indicator may be attached to the product by squeezing the product material, such as a plastic bag, into the indicator, if the indicator is rigid and comprising a fastening mechanism, such as shown in FIGS. 8 and 9, or by bending the indicator around the plastic bag, if the indicator is a flexible element which may be bent. The bag closure time-temperature indicator may advantageously be activated and attached to the packaging using a regular or modified bag closing machine. The device may advantageously be activated in the process of attaching to the product packaging material in order to provide the best indication of the time and temperature exposure for the product.

The device may provide a visual response with time and temperature exposure, such visual response preferably being a color change. Further, the device may provide an irreversible or substantially irreversible response of said time and temperature exposure.

The device may be suitable for all products currently being closed with ordinary bag closure devices or bag seals, i.e. bakery goods, such as bread or hotdog buns, fruits, and a variety of other products capable of being closed with bag closure devices.

One embodiment is a combination, comprising a bag closure device and a time-temperature indicator system (FIG. 8, FIG. 9), said time-temperature indicator system comprising a first compartment adjacent to a separate second compartment; said first compartment comprising at least one agent which changes visual appearance upon reduction; said second compartment comprising at least one mobile agent; said first and second compartments initially being separated by suitable means for preventing contact between the at least one agent which changes visual appearance upon reduction and the at least one mobile agent; the system being activated by bringing said two compartments into contact and thereby allow for the at least one mobile agent to migrate into the first compartment; with the proviso that i) at least one of said mobile agents is a pH modifying agent; and
  said first compartment further comprises a mutarotational reducing agent; or
ii) at least one of said mobile agents is a mutarotational reducing agent.

The time-temperature indicator system according to the present invention may be a full history time-temperature indicator system, a partly history time-temperature indicator system or a combination thereof.

As used herein, "a time-temperature indicator system which is both a full and partly history time-temperature indicator system" is intended to include a system which is classified as a full history time-temperature indicator system within specific temperature range(s) while being classified as a partly history time-temperature indicator system outside these temperature range(s). This is typically the case for a time-temperature indicator systems which comprises ingredients (e.g. water) which enters liquid to solid phase transitions (e.g. liquid to ice) at a certain temperature (e.g at 0° C.). Such a phase transition often results in drastic changes in the properties of the system including its response mechanisms.

Figure 4A:
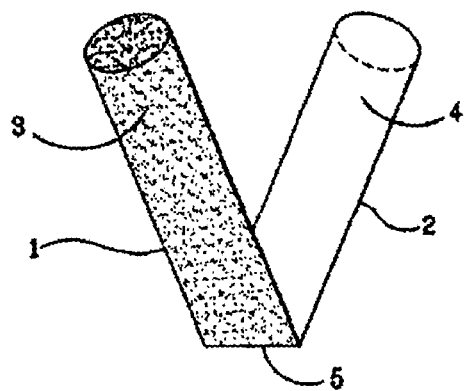
FIG. 4a illustrates a conceptual embodiment of the invention wherein the mobile agent and the agent which changes visual appearance upon reduction (3 and 4) are contained in a cylinder element including two compartments (1 and 2), and a sealing (5) between the two compartments (1 and 2) which is provided by bending the cylinder element.
Figure 4B:
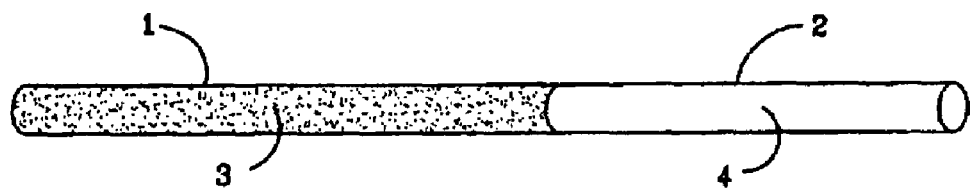
FIG. 4b illustrates the embodiment shown in FIG. 1a, wherein the seal has been removed by unbending the cylinder element.
Figure 5:
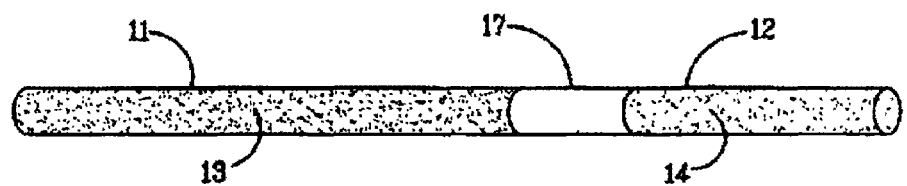
FIG. 5 illustrates a conceptual embodiment of the invention wherein the mobile agent and the agent which changes visual appearance upon reduction (13 and 14) are contained in a cylinder element including two compartments (11 and 12) and the sealing between the two compartments (11 and 12) is provided by a barrier (17).

The time-temperature indicator system according to the invention can advantageously be a system wherein the agents are contained in a cylinder element (FIGS. 4a, 4b and 5) or a rectangular strip shaped element (FIGS. 6 and 7) consisting of two compartments separated by means for preventing contact between the at least one mobile agent and the at least one agent which changes visual appearance upon reduction. Such a cylinder element or rectangular strip shaped element can be made of different materials such as glass and polymeric materials. Such a polymeric material can e.g. be polyethylene.

The suitable means for preventing contact between the at least one mobile agent and the at least one agent which changes visual appearance upon reduction may be provided by bending the time-temperature indicator system to occlude the transition between the compartments or it may be provided by a barrier such as thin polymer film. The barrier may also be provided by means of a material such as e.g. a wax, which is solid within a certain temperature range, but flows when a given threshold temperature is exceeded.

The system is typically activated by breaking or removing the sealing between the two compartments containing the agents. The breaking can e.g. be performed by means of exposing the sealing to mechanical stress, irradiation or heat. In the case the suitable means for preventing contact between the at least one mobile agent and the at least one agent which changes visual appearance upon reduction is provided by bending the time-temperature indicator system, the system is typically activated by unbending the time-temperature indicator system.

In a presently preferred embodiment of the invention as described herein, the time-temperature system yield a temperature sensitivity calculated to be in the range 12-50 kcal/mole (such as e.g. in the range 12-40 kcal/mole or 12-30 kcal/mole), more preferably in the range 14-50 kcal/mole (such as e.g. in the range 14-40 kcal/mole or 14-30 kcal/mole), even more preferably in the range 16-50 kcal/mole (such as e.g. in the range 16-40 kcal/mole or 16-30 kcal/mole) and most preferably in the range 20-50 kcal/mole (such as e.g. in the range 20-40 kcal/mole or 20-30 kcal/mole).

In one embodiment, said temperature sensitivity preferably being based on data obtained at i) 2, 4 and 8° C.; ii) 6, 12 and 16° C.; iii) 12, 24 and 48° C.; or iv) 24, 48 and 96° C.

There are a number of ways to calculate the temperature sensitivity of the time-temperature system according to the present invention. If not otherwise specified, the above temperature sensitivity data are calculated according to the methods described by T. P. Labuza (Journal of Chemical Education, Volume 61, Number 4, April 1984).

A particularily preferred embodiment according to the present invention relates to a time-temperature indicator system, preferably a system wherein the agents are contained in a cylinder element or a rectangular strip shaped element, comprising a first compartment adjacent to a separate second compartment; said first compartment comprising at least one agent which changes visual appearance upon reduction; said second compartment comprising at least one mobile agent; said first and second compartments initially being separated by suitable means for preventing contact between the at least one agent which changes visual appearance upon reduction and the at least one mobile agent; the system being activated by bringing said two compartments into contact and thereby allow for the at least one mobile agent to migrate into the first compartment; wherein the agent which changes visual appearance upon reduction is starch-complexed iodine which upon reduction looses its intense color;

the mobile agent is a mutarotational reducing sugar; preferably fructose; and the pH of the first compartment prior to activation being in the range 4-9 and the pH of the second compartment being in the range 8-12, more preferably in the range 9-11.

Another particularily preferred embodiment according to the present invention relates to a time-temperature indicator system, preferably a system wherein the agents are contained in a cylinder element or a rectangular strip shaped element, comprising a first compartment adjacent to a separate second compartment; said first compartment comprising at least one agent which changes visual appearance upon reduction; said second compartment comprising at least one mobile agent; said first and second compartments initially being separated by suitable means for preventing contact between the at least one agent which changes visual appearance upon reduction and the at least one mobile agent; the system being activated by bringing said two compartments into contact and thereby allow for the at least one mobile agent to migrate into the first compartment; wherein the agent which changes visual appearance upon reduction is starch-complexed iodine which upon reduction looses its intense color;

the first compartment further comprising a mutarotational reducing sugar; preferably fructose;

prior to activation the pH of the first compartment is in the range 4-8;

the mobile agent being a pH modifying agent which upon exposure to the first compartment rises the pH >8.

Said cylinder element or rectangular strip shaped element can be made of different materials such as glass and polymeric materials. Such a polymeric material can e.g. be polyethylene.

The suitable means for preventing contact between the at least one mobile agent and the at least one agent which changes visual appearance upon reduction may be provided by bending the time-temperature indicator system to occlude the transition between the compartments or it may be provided by a barrier such as thin polymer film. The barrier may also be provided by means of a material such as e.g. a wax, which is solid within a certain temperature range, but flows when a given threshold temperature is exceeded.

A third aspect of the present invention relates to a time-temperature indicator system, comprising an absorptive material; wherein at least one agent which changes visual appearance upon reduction has been absorbed to said absorptive material; the system being activated by absorbing at least one mutarotational reducing agent to said absorptive material.

In one preferred embodiment according to the third aspect of the present invention, the pH of the system prior to activation being >8, more preferably >9, even more preferably >10. In another embodiment, a pH modifying agent is also absorbed to said absorptive material resulting in a pH >8, more preferably >9, even more preferably >10 after activation.

A fourth aspect of the present invention relates to a time-temperature indicator system, comprising an absorptive material; wherein at least one mutarotational reducing agent and at least one agent which changes visual appearance upon reduction have been absorbed to said absorptive material; the system being activated by absorbing at least one pH modifying agent.

In one preferred embodiment according to the fourth aspect of the present invention, the pH of the system prior to activation being <9. In one preferred embodiment, said pH modifying agent sees to that the pH of the system after activation is >8, more preferably >9, even more preferably >10.

Said absorptive material preferably being paper, e.g. filter paper; or polymeric absorbant materials, e.g. rayon, polyester, PP, etc. Said absorptive material preferably being fibrous, porous, fiberlike, knitted, spun or perforated in structure. Said absorptive material may also be dried, or partly dried, polymer matrix comprising a gelling and/or non-gelling polymer which has absorptive functionality.

A particularly preferred embodiment according to the third aspect of the present invention relates to a time-temperature indicator system, comprising a piece of starch-containing paper; wherein iodine dissolved in an aqueous solution of iodide is absorbed to said piece of paper; the system being activated by absorbing at least one mutarotational reducing agent, preferably a reducing sugar such as glucose, to said paper; the pH of the system prior to activation preferably being >8.

A particularly preferred embodiment according to the fourth aspect of the present invention relates to a time-temperature indicator system, comprising a piece of starch-containing paper; wherein at least one mutarotational reducing agent, preferably a reducing sugar such as glucose, and iodine dissolved in an aqueous solution of iodide are absorbed to said piece of paper; the system being activated by absorbing at least one pH modifying agent, such as a carbonate buffer; the pH of the system prior to activation preferably being <9; the pH of the system after activation preferably being >8, more preferably >9, even more preferably >10.

The compartments or the absorptive layer of the system may be of variable dimensions i.e. either compartment can be triangular, wave-shaped, curved, sinusoidal, leaf like; circular, oval, elliptical; cylindrical (FIGS. 4a, 4b and 5); rectangular (FIGS. 6 and 7) pentagonic, diamond, teardropped, trapezoidal, symmertrical or non-symmertical; or any combination thereof.

The size of the compartments or the absorptive layer may be variable i.e. either compartment can have a length of up to 4 mm; 8 mm; 20 mm; 30 mm; 40 mm or above; with width of up to 1 mm; 2 mm; 4 mm; 6 mm; 8 mm; 10 mm; or above; with height of up to 0.1 mm; 0.5 mm; 1 mm; 2 mm; 4 mm; or above. For a circular system the diameter may be equal to the lengths indicated.

The matrix weight of either compartment may be of variable weight, ie. up to 10 mg, up to 20 mg; up to 40 mg; up to 80 mg; up to 160 mg; up to 320 mg; or higher.

The reaction front of the system is preferably visually clear and distinct, such that there is a low chance of misinterpretation of the reaction front. A visually defined front may be defined such that the full color change of the visual interface (front) occurs within less than 4 mm, less than 2 mm; less than 1 mm, less than 0.5 mm; less than 0.25 mm; or less than 0.1 mm.

The third and fourth aspect of the present invention are illustrated in example 4 and 5.

The invention will now be described by way of illustration in the following non-limiting examples.

EXAMPLES

The following examples are meant to illustrate how to make and use the invention. They are not intended to limit the scope of the invention in any manner or to any degree.

Example 1

Time-Temperature Indicator System A

Preparing the Content which are to be Included in the First Compartment (Gel-Strip)

90 mL of distilled water was added 1 gram of agar agar (final concentration 1% (weight/volume)) and 1 gram of starch (final concentration 1% (weight/volume)). The solution was heated to 100° C. for 5 minutes. After cooling to 60° C., 5 mL of an aqueous solution containing 0.1 M iodine ($I_2$) and 0.3 M potassium iodide (KI) was added. The volume of the mixture was adjusted to 100 mL by adding distilled water and then kept at a temperature of 50° C. until it was used.

Preparing the Content which are to be Included in the Second Compartment (Reservoir)

55 mL of distilled water was added 1 gram of agar agar (final concentration 1% (weight/volume)). The solution was heated to 100° C. for 5 minutes. After cooling to 60° C., 40 mL of a carbonate buffer consisting of 0.18 M sodium bicarbonate and 0.12 M of sodium carbonate was added. When the temperature of the mixture had reached 50° C. 0.6 gram of fructose was added. The volume of the mixture was adjusted to 100 mL by adding distilled water and then kept at a temperature of 50° C. until it was used. The results recorded for this example are shown in FIG. 1.

As can be seen from FIG. 1, this time-temperature indicator system provides in particular a system with high temperature sensitivity for long shelf life products.

Example 2

Time-Temperature Indicator System B

The solutions where prepared according to example a) with the following concentrations of the chemicals. The gel strip consists of 1% (weight/volume) agar agar, 1% (weight/volume) starch, 5 mM iodine ($I_2$), and 15 mM potassium iodide (KI) dissolved in water. The reservoir consists of 1% (weight/volume) agar agar, water, 0.24 M sodium bicarbonate, 0.16 M disodium carbonate, and 2% (weight/volume) fructose. The results recorded for this example are shown in FIG. 2.

Figure 2:
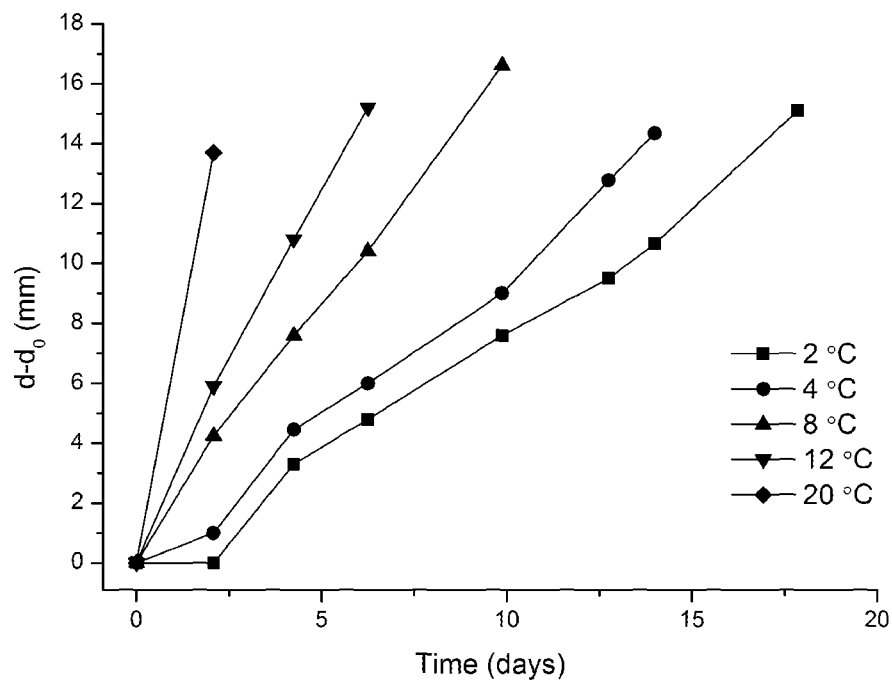
FIG. 2 illustrates the time-temperature sensitivity of the system at specific temperatures and how the time-temperature sensitivity changes with temperature. Y-axis: Position of the moving front "d" which is given with reference to the initial boundary between the second compartment and the first compartment "$d_0$". X-axis: Number of days.

As can be seen from FIG. 2, this time-temperature indicator system provides in particular a system with medium temperature sensitivity for medium shelf life products.

Example 3

Time-Temperature Indicator System C

The solutions where prepared according to example a) except that fructose was added to the gel strip solution after cooling it to 50° C. The following concentrations of the chemicals was used. The gel strip consists of 1% (weight/volume) agar agar, 1% (weight/volume) starch, 5 mM iodine ($I_2$), and 15 mM potassium iodide (KI), and 2% (weight/volume) fructose dissolved in water. The reservoir consists of 1% (weight/volume) agar agar, water, 0.24 M sodium bicarbonate, and 0.16 M disodium carbonate. The results recorded for this example are shown in FIG. 3.

Figure 3:
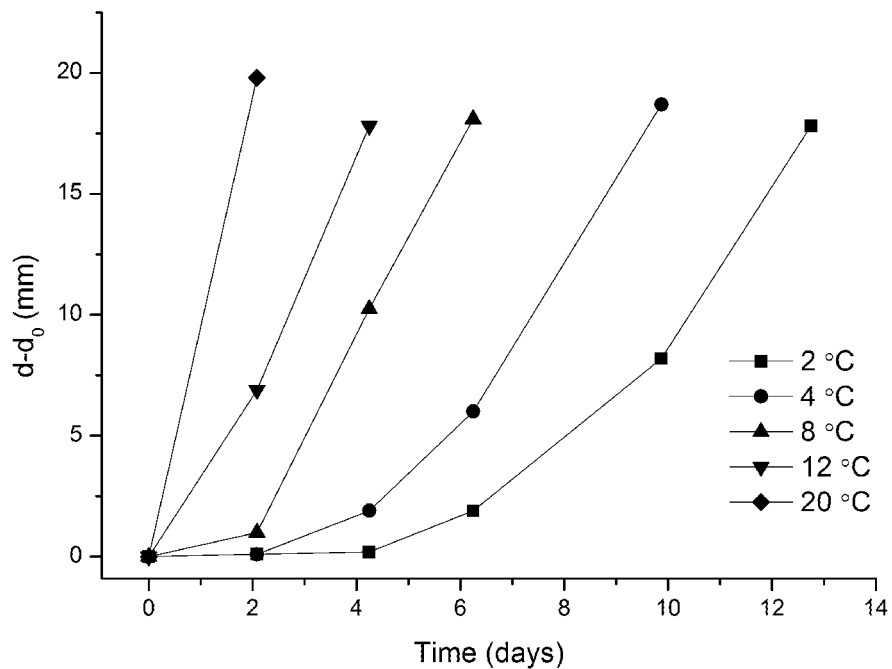
FIG. 3 illustrates the time-temperature sensitivity of the system at specific temperatures and how the time-temperature sensitivity changes with temperature. Y-axis: Position of the moving front "d" which is given with reference to the initial boundary between the second compartment and the first compartment "$d_0$". X-axis: Number of days.

As can be seen from FIG. 3, this time-temperature indicator system provides in particular a system with high temperature sensitivity for short shelf life products.

Example 4

Time-Temperature Indicator System D

A slice of starch containing paper was soaked in 5 mM iodine ($I_2$), and 15 mM potassium iodide (KI) dissolved in water. After drying, the stained paper was cut into circular slices of 4 mm in diameter. The button-indicator was activated by soaking the iodine stained slice of paper with a solution containing water, 0.3 M sodium bicarbonate, 0.2 M disodium carbonate, and 1% (weight/volume) fructose. The results recorded for this example are summarized in Table 1.

TABLE 1

| Data for an paper based time-temperature indicator button | | | | | |
|---|---|---|---|---|---|
| | Time required for complete color fading at different temperatures (hours) | | | | |
| Temperature | 2° C. | 4° C. | 8° C. | 12° C. | 20° C. |
| Example e) | 130-140 | 45-55 | 20-30 | 10-15 | 2.5 |

Example 5

Time-Temperature Indicator System E

A gel, prepared according to example a) containing 1% (weight/volume) agar agar, 1% (weight/volume) starch, 5 mM iodine ($I_2$), and 15 mM potassium iodide (KI) dissolved in water, was sliced into 1 mm thin circular segments. The button-indicator was activated by soaking the slice of gel with a solution containing water, 0.3 M sodium bicarbonate, 0.2 M disodium carbonate, and 1% (weight/volume) fructose.

Example 6

Time-Temperature Indicator System F

Preparation of Type A Gelatin Solution 500 grams of gelatine Type A was dissolved in 4.5 kg distilled water at a temperature of 90° C. The gelatin solution was then stored at 45° C. for 16-24 hours before use.

Preparation of Iodinated Type A Gelatin Solution 500 grams of gelatine Type A was dissolved in 4.5 kg distilled water at a temperature of 90° C. After cooling the solution to 65° C., 200 mL 0.5 M $I_2$, 1 M KI was added while stirring rigorously. Then, after stirring for 5 minutes, 100 mL of a carbonate buffer consisting of 0.75 M sodium bicarbonate and 0.75 M of sodium carbonate was added and stirring was continued for 30 minutes. The iodinated gelatin solution was finally stored at 45° C. for 16-24 hours before use.

Preparing the Content which are to be Included in the First Compartment (Gel-Strip)

1500 grams of distilled water was added 26 gram of starch and boiled for 10 minutes. After cooling to 40° C., 900 grams of iodinated gelatin, having a temperature of 40° C., was added while stirring carefully. Then 200 grams of a 0.1 M $I_2$, 0.6 M KI solution was added while stirring. Finally, 20 mL of distilled water containing 8 grams of $TiO_2$ was added. The solution was then kept at a temperature of 40° C. until it was used.

Preparing the Content which are to be Included in the Second Compartment (Reservoir)

700 grams of a room temperature carbonate buffer consisting of 0.75 M sodium bicarbonate and 0.75 M of sodium carbonate distilled water was added 190 grams of boiling distilled water. Then 48 grams of fructose was added and dissolved in the buffer water mixture. Finally, 450 grams of Type A gelatin solution (preparation described above) was added while carefully stirring. The solution was then kept at a temperature of 40° C. until it was used.

Figure 10:
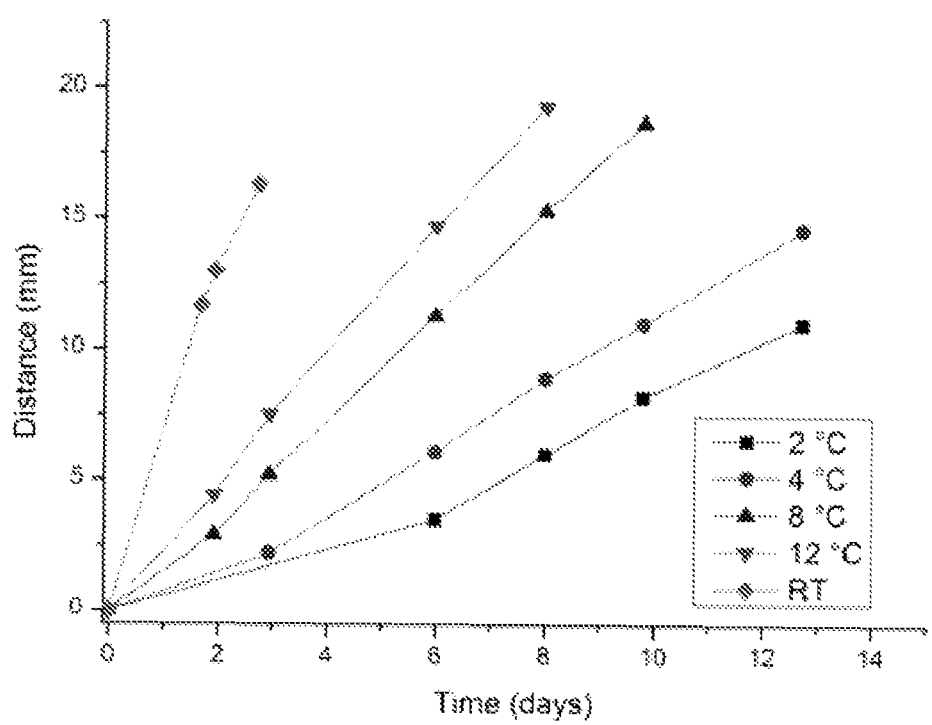
FIG. 10 illustrates the time-temperature sensitivity of the system at specific temperatures and how the time-temperature sensitivity changes with temperature. Y-axis: Position of the moving front "distance" which is given with reference to the initial boundary between the second compartment and the first compartment. X-axis: Number of days. RT is an abbreviation for room temperature (20-25° C., with an average of about 23° C.).

The results recorded for this example are shown in FIG. 10.

As can be seen from FIG. 10, this time-temperature indicator system provides in particular a system with high temperature sensitivity for medium to long shelf life products.

Example 7

Time-Temperature Indicator System G

Preparing the Content which are to be Included in the First Compartment (Gel-Strip)

2300 grams of distilled water was added 26 gram of starch and boiled for 10 minutes. After cooling to 80° C., 100 grams refined locust bean gum was added using a high shear mixer. When the temperature of the mixture reached 25° C., 200 grams of a 0.1 M $I_2$, 0.6 M KI solution was added while mixing using a high shear mixer. Finally, 20 mL of distilled water containing 8 grams of $TiO_2$ was added. The solution was then kept at a temperature of 20° C. until it was used.

Preparing the Content which are to be Included in the Second Compartment (Reservoir)

700 grams of a room temperature carbonate buffer consisting of 0.75 M sodium bicarbonate and 0.75 M of sodium carbonate distilled water was added 190 grams of boiling distilled water. Then 48 grams of fructose was added and dissolved in the buffer water mixture. Finally, 450 grams of 8% (w/w) homogenized locust bean gum—water solution was mixed with the fructose carbonated solution using a high shear mixer. The solution was then kept at a temperature of 20° C. until it was used.

We claim:

1. Time-temperature indicator system, comprising a first compartment adjacent to a separate second compartment; said first compartment comprising at least one agent which changes visual appearance upon reduction; said second compartment comprising at least one mobile agent; said first and second compartments initially being separated by a sealing for preventing contact between the at least one agent which changes visual appearance upon reduction and the at least one mobile agent; the system being activated by bringing said two compartments into contact and thereby allowing for the at least one mobile agent to migrate into the first compartment; with the proviso that
   i) at least one of said mobile agents is a pH modifying agent; and
      said first compartment further comprises a mutarotational reducing agent; or
   ii) at least one of said mobile agents is a mutarotational reducing agent.

2. Time-temperature indicator system according to claim 1, wherein a matrix is contained within said first compartment.

3. Time-temperature indicator system according to claim 2, wherein said matrix comprises at least a first matrix component.

4. Time-temperature indicator system according to claim 3, wherein said first matrix component is a gel-forming polymer, a gum or a paste.

5. Time-temperature indicator system according to claim 4, wherein said gum is selected from the group consisting of locust bean gum, xanthan gum, guar gum, gum arabic, gum ghatti, gum tragacanth; and said paste is selected from the group consisting of petroleum jelly with zinc oxide, clay and silica gel paste.

6. Time-temperature indicator system according to claim 2, wherein said matrix comprises locust bean gum.

7. Time-temperature indicator system according to claim 1, wherein at least one of said mobile agents is a pH modifying agent; and said first compartment further comprises a mutarotational reducing agent.

8. Time-temperature indicator system according to claim 7, wherein
   the pH in said first compartment prior to activation is <9; and
   the pH in said second compartment prior to activation is >8 but always higher than the pH in the first compartment prior to activation.

9. Time-temperature indicator system according to claim 1, wherein at least one of said mobile agents is a mutarotational reducing agent.

10. Time-temperature indicator system according to claim 9, wherein
    the pH in said first compartment prior to activation is >8; or
    the pH in said first compartment prior to activation is <9 and the pH in said second compartment prior to activation is >8 but always higher than the pH in the first compartment prior to activation.

11. Time-temperature indicator system according to claim 1, wherein said pH modifying agent is an alkaline buffer, preferably a carbonate buffer such as e.g. sodium carbonate buffer or a potassium carbonate buffer.

12. Time-temperature indicator system according to claim 1, wherein the agent which changes visual appearance upon reduction is a starch-iodine complex.

13. A combination, comprising the system according to claim 1 and a product storage container or a bag closure device.

14. A method for producing the time-temperature indicator system according to claim 1, the method comprising the following steps:
 i) forming at least a first and a second separate compartments in a plastic sheet layer,
 ii) filling said first compartment with a composition comprising an agent which changes visual appearance upon reduction;
 iii) filling said second compartment with a composition comprising the mobile agent(s) defined in claim 1;
 iv) sealing said compartments by a second layer;
 v) optionally, activating said device by selectively compressing at least one compartment formed by the two layers thus bringing the two compartments into contact.

15. Time-temperature indicator system comprising an absorptive material, wherein
 at least one agent which changes visual appearance upon reduction has been absorbed to said absorptive material; the system being activated by absorbing at least one mutarotational reducing agent to said absorptive material; or
 at least one mutarotational reducing agent and at least one agent which changes visual appearance upon reduction have been absorbed to said absorptive material; the system being activated by absorbing at least one pH modifying agent.

* * * * *